United States Patent
Mako

(10) Patent No.: US 9,425,635 B2
(45) Date of Patent: Aug. 23, 2016

(54) RADIATION IMAGING APPARATUS, AND CONTROL METHOD AND PROGRAM THEREFOR

(71) Applicant: CANON KABUSHIKI KAISHA, Tokyo (JP)

(72) Inventor: Yuta Mako, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 820 days.

(21) Appl. No.: 13/858,321

(22) Filed: Apr. 8, 2013

(65) Prior Publication Data

US 2013/0270913 A1    Oct. 17, 2013

(30) Foreign Application Priority Data

Apr. 13, 2012 (JP) ................. 2012-092169

(51) Int. Cl.
*H02J 7/00* (2006.01)
*H02J 9/00* (2006.01)
*A61B 6/00* (2006.01)

(52) U.S. Cl.
CPC . *H02J 7/007* (2013.01); *A61B 6/56* (2013.01); *H02J 7/0055* (2013.01); *H02J 7/0068* (2013.01); *H02J 9/00* (2013.01); *H02J 2007/005* (2013.01); *Y10T 307/625* (2015.04)

(58) Field of Classification Search
CPC ........... H02J 7/007; H02J 9/00; H02J 7/0055; H02J 7/0068; H02J 2007/005; A61B 6/56; Y10T 307/625
See application file for complete search history.

(56) References Cited

U.S. PATENT DOCUMENTS

| | | | | |
|---|---|---|---|---|
| 6,756,767 B2* | 6/2004 | Kawai | ............... | H02J 7/0075 320/125 |
| 8,248,032 B2* | 8/2012 | Ozeki | ............... | H02J 7/0018 320/124 |
| 8,532,261 B2* | 9/2013 | Kamiya | ............... | A61B 6/4283 378/102 |
| 8,886,479 B2* | 11/2014 | Matsumoto | ......... | B60L 11/123 320/106 |
| 2010/0232575 A1* | 9/2010 | Hall | ................. | A61B 6/4233 378/189 |

FOREIGN PATENT DOCUMENTS

| JP | 3494683 B | 2/2004 |
|---|---|---|
| JP | 2009-237230 A | 10/2009 |
| JP | 2011-203595 A | 10/2011 |

OTHER PUBLICATIONS

Japanese Office Action issued in corresponding application No. 2012092169 on Feb. 2, 2016.

* cited by examiner

*Primary Examiner* — Zeev V Kitov
(74) *Attorney, Agent, or Firm* — Carter, DeLuca, Farrell & Schmidt, LLP

(57) ABSTRACT

A radiation imaging apparatus taking an image data of a subject by detecting radiations having passed through the subject, includes a charging control unit configured to control a battery internally attached to the radiation imaging apparatus such that a first charge amount up to which the battery is charged using an external power source connected to the radiation imaging apparatus is different from a second charge amount up to which the battery is charged using an external apparatus.

8 Claims, 3 Drawing Sheets

| CHARGE STATE | CHARGE? YES OR NO (INTERNAL CHARGE DETERMINATION UNIT) | POWER SUPPLY MEANS (DRIVE POWER SOURCE DETERMINATION UNIT) |
|---|---|---|
| CHARGE-UNNECESSARY STATE (71% TO 100%) | NO | INTERNAL BATTERY |
| CHARGE-FREE BEST STATE (50% TO 70%) | NO | EXTERNAL POWER SOURCE |
| CHARGE-NECESSARY STATE (0% TO 49%) | YES | EXTERNAL POWER SOURCE |

RADIATION IMAGING APPARATUS, AND CONTROL METHOD AND PROGRAM THEREFOR

BACKGROUND OF THE INVENTION

1. Field of the Invention

The present invention relates to a technique of charging a battery internally attached to a radiation imaging apparatus.

2. Description of the Related Art

Conventionally, an X-ray image taken using radiations, such as X-rays, has been widely used for disease diagnosis. Furthermore, an X-ray imaging apparatus has been commercialized that applies image processing to an X-ray image taken by the X-ray imaging apparatus and generates a clearer X-ray image. When an X-ray image is taken, the X-ray imaging apparatus is typically installed on one of a mount and a bed in a fixed manner. However, to increase installation flexibility of the X-ray imaging apparatus on imaging, in some cases, the X-ray imaging apparatus is not mechanically fixed but takes an image at a free position instead. As an example to meet such requirements, for instance, Japanese Patent No. 3,494,683 discloses an X-ray imaging apparatus that adopts wireless communication to increase installation flexibility on imaging.

Adoption of wireless communication for increasing the installation flexibility of the X-ray imaging apparatus on imaging requires a battery in the X-ray imaging apparatus (hereinafter, called an internal battery). A rechargeable internal battery capable of being repeatedly used can be employed. Schemes of charging an internal battery include a dedicated charger scheme in which an internal battery is removed from an X-ray imaging apparatus, the battery is attached to a dedicated charger and the charger charges the battery, and a main body charging scheme in which an internal battery is charged in a state where the battery is attached to an X-ray imaging apparatus and a power source cable is connected to the X-ray imaging apparatus.

The dedicated charger scheme and the main body charging scheme have their own advantages. The advantage of the dedicated charger scheme is that, while the X-ray imaging apparatus is used through wireless communication, another internal battery can be charged independently and in parallel. That is, when the power of the internal battery used in the X-ray imaging apparatus is lost, the battery is replaced with another internal battery having been charged independently in parallel, thereby allowing the operation of taking an X-ray image to be immediately restarted. The advantage of the main body charging scheme is that, in the case where use of the X-ray imaging apparatus through wireless communication is not specifically required, the power source cable is connected to the X-ray imaging apparatus and the apparatus is used through wired communication, thereby allowing the operation of taking an X-ray image while charging the internal battery without consuming power accumulated in the internal battery. Thus, the dedicated charger scheme and the main body charging scheme have their own advantages. The X-ray imaging apparatus is required to have both functions of the dedicated charger scheme and the main body charging scheme.

In the X-ray imaging apparatus having the functions of both the dedicated charger scheme and the main body charging scheme, electric circuits and an X-ray sensor of which temperatures increase by power consumption are enclosed in a sealed housing because of necessity to block external light. Accordingly, in some cases, the temperature becomes as high as more than 50° C. It is known that, if the internal battery is left in a state of being at a high temperature and fully charged, deterioration of the internal battery is enhanced to reduce the life thereof. However, conventionally, in operation of the X-ray imaging apparatus, even though the internal temperature becomes high, the internal battery is sometimes left in a state of being fully charged. Accordingly, deterioration of the internal battery is enhanced. As a result, a time for taking an X-ray image is unfortunately reduced. In order to remove such troubles, the present invention which can prevent the battery from deteriorating and increase the battery life is provided.

SUMMARY OF THE INVENTION

A radiation imaging apparatus according to the present invention is a radiation imaging apparatus taking an image data of a subject by detecting radiations having passed through the subject, the apparatus including a charging control unit configured to control a battery internally attached to the radiation imaging apparatus such that a first charge amount up to which the battery is charged using an external power source connected to the radiation imaging apparatus is different from a second charge amount up to which the battery is charged using an external apparatus.

Further features of the present invention will become apparent from the following description of exemplary embodiments with reference to the attached drawings.

DESCRIPTION OF THE EMBODIMENTS

An exemplary embodiment to which the present invention is applied will hereinafter be described in detail with reference to accompanying drawings.

A first embodiment of the present invention will be described. In the first embodiment, a difference in charge amount is provided between the dedicated charger scheme and the main body charging scheme. That is, in the case of charging by the dedicated charger scheme, the internal battery is charged up to the maximum charge amount of this battery. In the case of charging by the main body charging scheme, the internal battery is not charged up to the maximum charge amount of this battery.

Figures 1, 2:
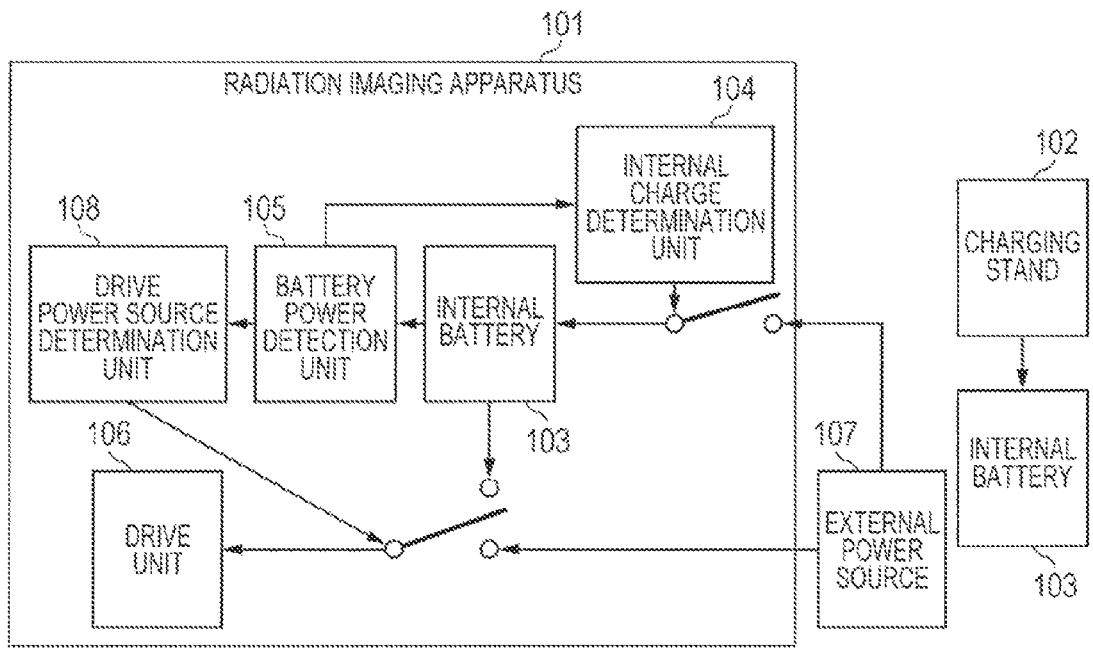
FIG. 1 illustrates a configuration of a radiation imaging apparatus according to a first embodiment of the present invention.
FIG. 2 illustrates relationship between a remaining power of an internal battery and determination results of an internal charge determination unit and a drive power source determination unit.

FIG. 1 illustrates a configuration of a radiation imaging apparatus according to a first embodiment of the present invention. As illustrated in FIG. 1, the radiation imaging apparatus 101 according to the first embodiment includes an internal battery 103, an internal charge determination unit 104, a battery power detection unit 105, a drive unit 106 and a drive power source determination unit 108. As the radiation imaging apparatus 101 according to this embodiment, an apparatus is assumed that detects X-rays, a type of radiations, having passed through a subject, and generates a radiation image data. However, radiations that can be employed by the present invention are not limited to X-rays. Instead, the radiations may be another type of radiations that are any of α rays, β rays and γ rays.

The drive unit 106 drives an operation of detecting radiations having passed through the subject to generate the radiation image data. In the case where the radiation imaging apparatus 101 is used through wireless communication, the internal battery 103 supplies power to components in the radiation imaging apparatus 101, such as the drive unit 106, the internal charge determination unit 104, the battery power detection unit 105 and the drive power source determination unit 108. Meanwhile, in the case where the radiation imaging apparatus 101 is used through wired communication, the radiation imaging apparatus 101 is connected to the external power source 107 by a power source cable. The internal battery 103 is charged by power supplied by the external power source 107, while power is supplied from the external power source 107 to the drive unit 106 and so on. As described above, in this embodiment, in the case of charging by the dedicated charger scheme, that is, when the internal battery 103 is charged using the charging stand 102, the internal battery 103 is charged up to the maximum charge amount of this battery. Meanwhile, in the case of charging by the main body charging scheme, that is, when the internal battery 103 is charged using the external power source 107, the internal battery 103 is not charged up to the maximum charge amount of this battery.

When the internal battery 103 is mounted on the radiation imaging apparatus 101, or periodically, the battery power detection unit 105 detects the remaining power of the internal battery 103. The internal charge determination unit 104 determines whether to charge internal battery 103 or not based on the remaining power of the internal battery 103. That is, in the case of charging the internal battery 103 using the external power source 107, the internal charge determination unit 104 periodically acquires the remaining power of the internal battery 103 from the battery power detection unit 105. If the remaining power of the internal battery 103 is, for instance, 49% or less, the internal charge determination unit 104 determines to charge (start charging) the internal battery 103. In contrast, if the remaining power of the internal battery 103 is, for instance, 50% or more, the internal charge determination unit 104 determines not to charge (to finish charging) the internal battery 103. In the case of charging the internal battery 103 using the charging stand 102, the internal battery 103 is charged until the remaining power of this battery reaches, for instance, 100% (maximum charge amount). Meanwhile, in the case of charging the internal battery 103 using the external power source 107, the internal battery 103 is charged until the remaining power of this battery 103 reaches a predetermined remaining power (e.g., a range between 50 and 70%). The upper limit of the charge amount of the internal battery 103 in the case of such charging through use of the external power source 107 exemplifies a first charge amount. The upper limit of the charge amount of the internal battery 103 in the case of charging through use of the charging stand 102 exemplifies a second charge amount. Furthermore, the internal charge determination unit 104 and the battery power detection unit 105 are application examples of components of a charging control unit.

The drive power source determination unit 108 determines whether to supply power to the drive unit 106 and so on from the external power source 107 or from the internal battery 103, based on the remaining power of the internal battery 103 detected by the battery power detection unit 105. That is, if the remaining power of the internal battery 103 is, for instance, 71% or more, the drive power source determination unit 108 determines to supply power to the drive unit 106 and so on from the internal battery 103. If the remaining power of the internal battery 103 is, for instance, 70% or less, the drive power source determination unit 108 determines to supply power to the drive unit 106 and so on from the external power source 107. The numeric values of the remaining powers are exemplary values. The values are not limited to the above numeric values.

FIG. 2 is a table illustrates relationship between the remaining power of the internal battery 103 and determination results of the internal charge determination unit 104 and the drive power source determination unit 108. In this embodiment, if the remaining power of the internal battery 103 is in a range from 71% to 100%, the radiation imaging apparatus 101 (internal battery 103) is in a charge-unnecessary state. If the remaining power of the internal battery 103 is in a range from 50% to 70%, the radiation imaging apparatus 101 is in a charge-free best state. If the remaining power of the internal battery 103 is in a range from 0% to 49%, the radiation imaging apparatus 101 is in a charge-necessary state. Here, it is assumed that the temperature of the charging stand is a room temperature and the internal temperature of the radiation imaging apparatus is a temperature +15° C. higher than the room temperature.

As illustrated in FIG. 2, if the radiation imaging apparatus 101 is in the charge-unnecessary state, the internal charge determination unit 104 determines not to charge the internal battery 103 while the drive power source determination unit 108 determines to supply power to the drive unit 106 and so on from the internal battery 103. If the radiation imaging apparatus 101 is in the charge-free best state, the internal charge determination unit 104 determines not to charge the internal battery 103 while the drive power source determination unit 108 determines to supply power to the drive unit 106 and so on from the external power source 107. If the radiation imaging apparatus 101 is in the charge-necessary state, the internal charge determination unit 104 determines to charge the internal battery 103 while the drive power source determination unit 108 determines to supply power to the drive unit 106 and so on from the external power source 107.

Figure 3:
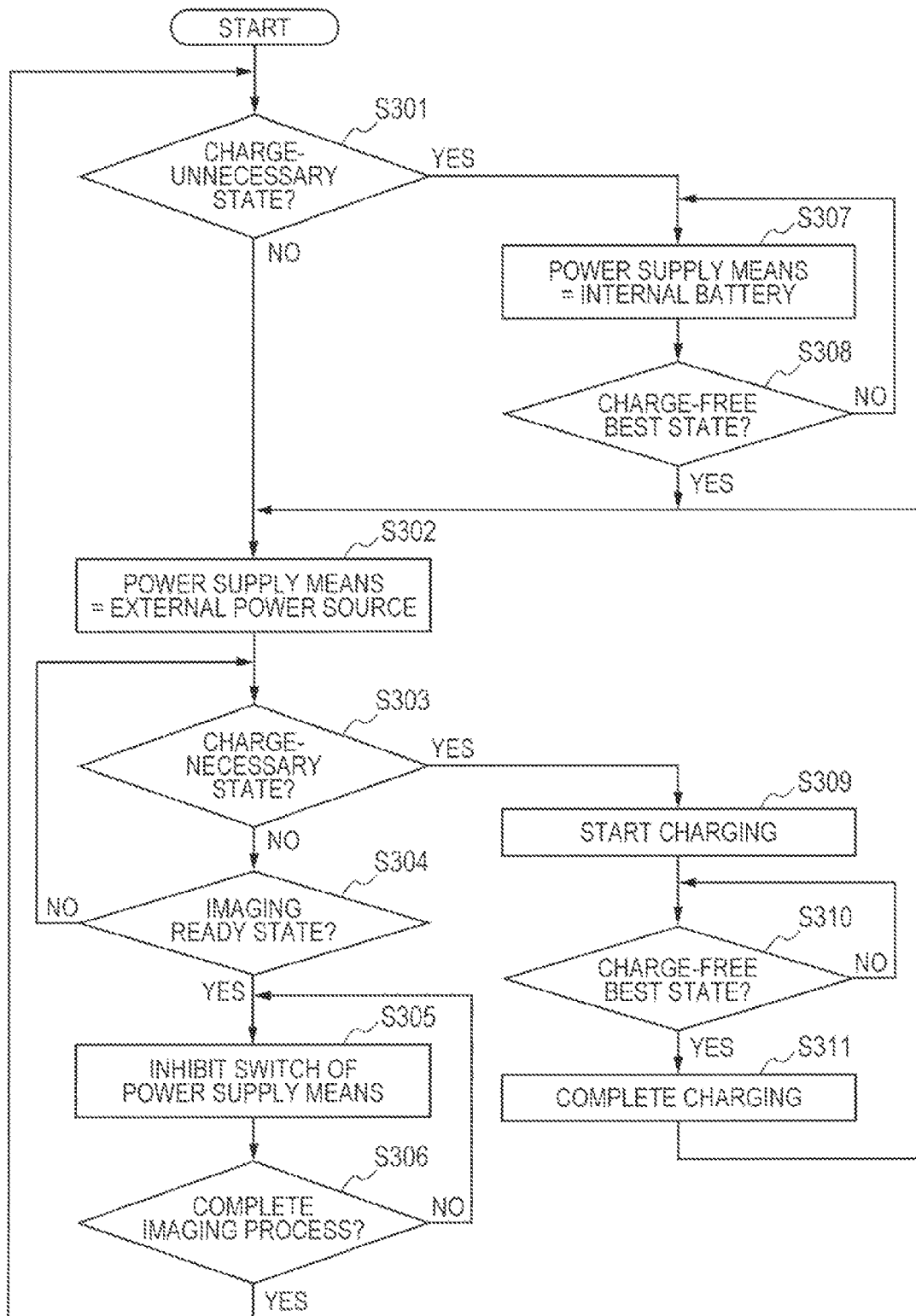
FIG. 3 is a flowchart illustrating processes of the radiation imaging apparatus according to the first embodiment of the present invention.

FIG. 3 is a flowchart illustrating processes of the radiation imaging apparatus 101 according to the first embodiment of the present invention. Hereinafter, referring to FIG. 3, the processes of the radiation imaging apparatus 101 according to this embodiment will be described. A CPU, not illustrated, in the radiation imaging apparatus 101 reads required data and programs from a storage medium, such as ROM, and executes the programs, thereby achieving the processes illustrated in FIG. 3.

In step S301, the drive power source determination unit 108 acquires the remaining power of the internal battery 103 from the battery power detection unit 105, and determines whether the radiation imaging apparatus 101 is in the charge-unnecessary state or not, based on the acquired remaining power of the internal battery 103. If the radiation imaging apparatus 101 is in the charge-unnecessary state, the processing proceeds to step S307. In contrast, if the radiation imaging apparatus 101 is not in the charge-unnecessary state, the processing proceeds to step S302.

In step S302, the drive power source determination unit 108 determines to supply power to the drive unit 106 and so on from the external power source 107. In step S303, the drive power source determination unit 108 determines whether the radiation imaging apparatus 101 is in the charge-necessary state or not, based on the remaining power of the internal battery 103 acquired from the battery power detection unit 105. If the radiation imaging apparatus 101 is in the charge-necessary state, the processing proceeds to step S309. In contrast, if the radiation imaging apparatus 101 is not in the charge-necessary state, the processing proceeds to step S304.

In step S304, the drive power source determination unit 108 determines whether the radiation imaging apparatus 101 is in an imaging ready state or not. If the radiation imaging apparatus 101 is in the imaging ready state, the processing proceeds to step S305. In contrast, if the radiation imaging apparatus 101 is not in the imaging ready state, the processing returns to step S303. In step S305, the drive power source determination unit 108 inhibits switch of power supply means. More specifically, change of a current power supply source (one of the internal battery 103 and the external power source 107) for the drive unit 106 and so on is inhibited.

In step S306, the drive power source determination unit 108 determines whether the radiation imaging apparatus 101 has completed the imaging process or not. If the imaging process has been completed, the processing returns to step S301. In contrast, if the imaging process has not been completed, the processing returns to step S305 and the state of inhibiting switch of the power supply means is maintained.

In step S307, the drive power source determination unit 108 determines to supply power to the drive unit 106 and so on from the internal battery 103. In step S308, the drive power source determination unit 108 determines whether the radiation imaging apparatus 101 is in the charge-free best state or not. If the radiation imaging apparatus 101 is in the charge-free best state, the processing proceeds to step S302. In contrast, the radiation imaging apparatus 101 is not in the charge-free best state, the processing returns to step S307.

In step S309, the internal charge determination unit 104 determines to charge the internal battery 103 (start charging the internal battery 103). Thus, the internal battery 103 is started to be charged using the external power source 107. In step S310, the internal charge determination unit 104 determines whether the radiation imaging apparatus 101 is in the charge-free best state or not. If the radiation imaging apparatus 101 is in the charge-free best state, the processing proceeds to step S311. In contrast, if the radiation imaging apparatus 101 is not in the charge-free best state, the processing returns to step S310. In step S311, the internal charge determination unit 104 determines not to charge the internal battery 103 (to complete charging of the internal battery 103). Thus, charging of the internal battery 103 using the external power source 107 has been completed. At this time, the remaining power of the internal battery 103 is in a range from 50% to 70%, and the internal battery is not charged up to the maximum charge amount of this battery. Subsequently, the processing returns to step S302.

As described above, in the first embodiment, the internal battery 103 is not left in the state of being at a high temperature and fully charged. Accordingly, the internal battery 103 can be prevented from deteriorating, and the life of the internal battery 103 can be increased.

Next, a second embodiment of the present invention will be described. Also in the second embodiment, in the case of charging by the dedicated charger scheme, the internal battery is charged up to the maximum charge amount of this battery. In the case of charging by the main body charging scheme, the internal battery is not charged up to the maximum charge amount of this battery.

Figure 4:
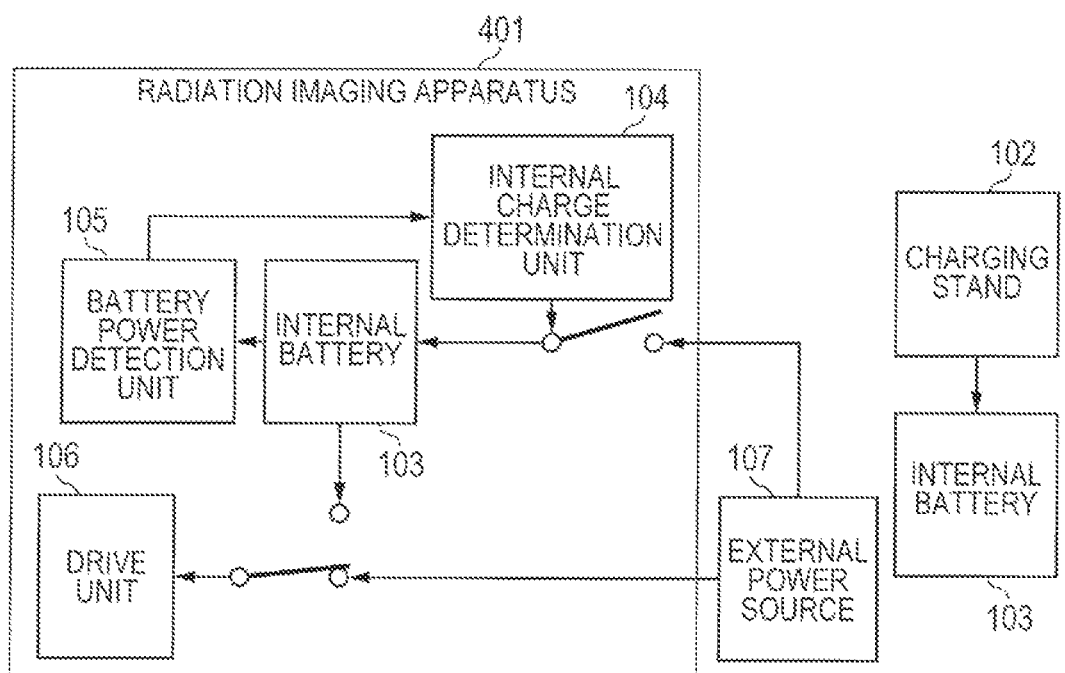
FIG. 4 illustrates a configuration of a radiation imaging apparatus according to a second embodiment of the present invention.

FIG. 4 illustrates a configuration of a radiation imaging apparatus according to the second embodiment of the present invention. As illustrated in FIG. 4, the configuration of the radiation imaging apparatus 401 according to the second embodiment is different from the configuration of the radiation imaging apparatus 101 according to the first embodiment illustrated in FIG. 1 in that the drive power source determination unit 108 is omitted. The other components are the same. That is, as with the first embodiment, the radiation imaging apparatus 401 according to the second embodiment starts charging the internal battery 103 using the external power source 107 when the remaining power of the internal battery 103 becomes 49% or less (in a charge-necessary state). If the remaining power of the internal battery 103 is in a range from 50% to 70% (in a charge-free best state), the radiation imaging apparatus 401 completes charging of the internal battery 103 using the external power source 107. However, the radiation imaging apparatus 401 according to the second embodiment does not perform the process of determining the power supply means to the drive unit 106 and so on based on the remaining power of the internal battery 103. Even such a simplified configuration can prevent the internal battery 103 from being left in the state where the internal battery 103 is at a high temperature and fully charged, as with the first embodiment. Accordingly, the internal battery 103 can be prevented from deteriorating, and the life of the internal battery 103 can be increased.

Other Embodiments

Embodiments of the present invention can also be realized by a computer of a system or apparatus that reads out and executes computer executable instructions stored on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-092169, filed on Apr. 13, 2012, which is hereby incorporated by reference herein in its entirety.

What is claimed is:

1. A radiation imaging apparatus taking image data of a subject by detecting radiation having passed through the subject, comprising:

a charging control unit configured to control a battery internally attached to the radiation imaging apparatus such that a first charge amount up to which the battery internally attached to the radiation imaging apparatus is charged using an external power source connected to the radiation imaging apparatus is different from a second charge amount up to which the battery in a state where the battery is unconnected to the radiation image apparatus is charged using an external apparatus.

2. The radiation imaging apparatus according to claim 1, wherein the first charge amount is less than the second charge amount.

3. The radiation imaging apparatus according to claim 1, wherein the charging control unit completes charging of the battery using the external power source, by detecting that a state of a charge of the battery in charging using the external power source reaches a predetermined state of the charge less than a maximum charge amount of the battery.

4. A method of controlling a radiation imaging apparatus taking image data of a subject by detecting radiation having passed through the subject, comprising:
  performing charging control of a battery internally attached to the radiation imaging apparatus such that a first charge amount up to which the battery internally attached to the radiation imaging apparatus is charged using an external power source connected to the radiation imaging apparatus is different from a second charge amount up to which the battery in a state where the battery is unconnected to the radiation image apparatus is charged using an external apparatus.

5. A non-transitory storage medium storing a computer program configured to cause a computer to execute a method of controlling a radiation imaging apparatus taking image data of a subject by detecting radiation having passed through the subject, the computer program causing the computer to execute:
  performing charging control of a battery internally attached to the radiation imaging apparatus such that a first charge amount up to which the battery internally attached to the radiation imaging apparatus is charged using an external power source connected to the radiation imaging apparatus is different from a second charge amount up to which the battery in a state where the battery is unconnected to the radiation image apparatus is charged using an external apparatus.

6. A radiation imaging apparatus taking image data of a subject by detecting radiation having passed through the subject, comprising:
  a power control unit configured
    to use a battery internally attached to the radiation imaging apparatus as a power supply source until the battery reaches a charge-free best state, if the battery is in a charge-unnecessary state, and
    to use an external power source as the power supply source, if the battery internally attached to the radiation imaging apparatus is not in the charge-unnecessary state; and
  a charging control unit configured to charge the battery until the battery reaches the charge-free best state, if the battery is in a charge-necessary state, and to inhibit charge of the battery, if the radiation imaging apparatus is in an imaging ready state.

7. A method of controlling a radiation imaging apparatus taking image data of a subject by detecting radiation having passed through the subject, comprising:
  performing power control such that
    a battery internally attached to the radiation imaging apparatus is used as a power supply source until the battery reaches a charge-free best state, if the battery is in a charge-unnecessary state, and
    an external power source is used as the power supply source, if the battery internally attached to the radiation imaging apparatus is not in the charge-unnecessary state; and
  performing charging control such that the battery is charged until the battery reaches the charge-free best state, if the battery is in a charge-necessary state, and that charge of the battery is inhibited, if the radiation imaging apparatus is in an imaging ready state.

8. A non-transitory storage medium storing a computer program configured to cause a computer to execute a method of controlling a radiation imaging apparatus taking image data of a subject by detecting radiation having passed through the subject, the computer program causing the computer to execute:
  performing power control of such that
    a battery internally attached to the radiation imaging apparatus is used as a power supply source until the battery reaches a charge-free best state, if the battery is in a charge-unnecessary state, and
    an external power source is used as the power supply source, if the battery internally attached to the radiation imaging apparatus is not in the charge-unnecessary state; and
  performing charging control such that the battery is charged until the battery reaches the charge-free best state, if the battery is in a charge-necessary state, and that charge of the battery is inhibited, if the radiation imaging apparatus is in an imaging ready state.

* * * * *